United States Patent [19]

Bodelin-LeComte

[11] Patent Number: 5,928,652
[45] Date of Patent: Jul. 27, 1999

[54] BINDER COMPOSITIONS COMPRISING AN ESTER AND THEIR USE

[75] Inventor: Sophie Bodelin-LeComte, Vanves, France

[73] Assignee: L'Oreal, Paris, France

[21] Appl. No.: 08/808,573

[22] Filed: Feb. 28, 1997

[30] Foreign Application Priority Data

Mar. 1, 1996 [FR] France .................................. 96 02627

[51] Int. Cl.$^6$ ...................................................... A61K 7/00
[52] U.S. Cl. ........................ 424/400; 424/401; 424/421; 424/498; 424/502; 424/46; 424/47; 424/59; 424/63; 424/65; 424/69
[58] Field of Search ................................... 428/363, 403; 424/400, 401, 420, 421, 485, 498, 502, 46, 47, 59, 63, 65, 69

[56] References Cited

U.S. PATENT DOCUMENTS

| | | | |
|---|---|---|---|
| 4,376,762 | 3/1983 | Hauschild et al. ........................ | 424/49 |
| 5,063,050 | 11/1991 | Verdon et al. . | |
| 5,356,617 | 10/1994 | Schlossman ............................... | 424/63 |
| 5,556,613 | 9/1996 | Arnaud et al. . | |

FOREIGN PATENT DOCUMENTS

| | | |
|---|---|---|
| 036199 | 9/1981 | European Pat. Off. . |
| 132631-A1 | 2/1985 | European Pat. Off. . |
| 665008 | 8/1995 | European Pat. Off. . |
| 60-042317 | 3/1985 | Japan . |
| 60-075405 | 4/1985 | Japan . |
| 60-075406 | 4/1985 | Japan . |
| 02088511 | 3/1990 | Japan . |
| 06128123 | 5/1994 | Japan . |
| 07228515 | 8/1995 | Japan . |
| 07258028 | 10/1995 | Japan . |
| WO9427560 | 12/1994 | WIPO . |

*Primary Examiner*—Neil S. Levy
*Attorney, Agent, or Firm*—Finnegan, Henderson, Farabow, Garrett & Dunner, L.L.P.

[57] ABSTRACT

The invention relates to a binder composition comprising:

(i) at least 20% by weight, relative to the total weight of the binder composition, of at least one ester which is liquid at room temperature comprising at least two hydrocarbon chains, each hydrocarbon chain independently containing at least 10 carbon atoms, the ester containing no hydroxyl groups and having a wettability ranging from 30 seconds to 10 minutes, (ii) the possible difference to 100% by weight, relative to the total weight of the binder composition, of at least one fatty substance which is compatible with the ester, in an anhydrous composition in powder form comprising at least one pulverulent compound, and its use as an agent for aiding the dispersion of the anhydrous composition in powder form and/or for improving the solidity and/or strength of an anhydrous composition in compact powder form.

24 Claims, No Drawings

BINDER COMPOSITIONS COMPRISING AN ESTER AND THEIR USE

The present invention relates to the use of certain esters as binders in compositions in powder form, as well as to a composition in powder form comprising at least one selected ester as binder. The composition according to the invention may be used in the cosmetic, dermatological, pharmaceutical and hygiene fields.

In the field of powdery cosmetic compositions, in the form of free or compact powders for making up the face or alternatively body powders, it is known to use, on the one hand, a particulate phase containing pigments and fillers in particular, and, on the other hand, a fatty phase as binder comprising fatty substances, which is intended to impart a certain density to the finished product, to give a certain cohesion to the inorganic and/or organic particles of the particulate phase, to give the make-up product softness and an emollient property and to promote its adhesion to the skin.

It is known to use as binders oils of petroleum or animal origin, or alternatively silicone oils, as described in U.S. Pat. No. 5,023,075, or fluoro oils as described in European patent application EP-A-469 602. Binders for compacted powders based on long-chain fatty acid esters, such as isocetyl stearate, are also described in U.S. Pat. No. 5,063,050.

However, the development of such compositions raises many difficulties since the final composition must be sufficiently homogeneous and compact to have a good capacity to be taken up and moreover to prevent fragmentation which may be brought about, in particular, by impacts.

Furthermore, in order to allow the application of a homogeneous product, it is necessary for the solid particles to be well-dispersed. However, the binders commonly used do not make it possible to obtain satisfactory dispersions of powders.

The object of the present invention is to overcome the drawbacks of the prior art and to provide a composition in compacted or cast powder form having a good dispersion of solid particles. Furthermore, when the composition is compact, it is of good cohesion: the composition thus obtained is more solid, more resistant to impacts and does not fragment easily.

The inventors have discovered, surprisingly and unexpectedly, that the dispersion of powders can be improved by using specific esters.

One subject of the invention is thus the use of a binder composition comprising:
  (i) at least 20% by weight, relative to the total weight of the binder composition, of at least one ester which is liquid at room temperature comprising at least two hydrocarbon chains, each hydrocarbon chain independently containing at least 10 carbon atoms, the said ester containing no hydroxyl groups and having a wettability ranging from 30 seconds to 10 minutes,
  (ii) the possible difference to 100% by weight, relative to the total weight of the binder composition, of at least one fatty substance which is compatible with the said ester, as an agent for aiding the dispersion of the powders.

Another subject of the invention is the use of the binder composition as described above in an anhydrous composition, in compact powder form, in order to improve the solidity and/or strength, in particular the impact strength, of the said anhydrous composition.

Another subject of the invention is an anhydrous composition in compacted or cast powder form comprising a binder and a pulverulent compound, characterized in that the binder comprises at least 90% by weight, relative to the total weight of binder in the composition, of a binder composition comprising:
  (i) at least 20% by weight, relative to the total weight of the binder composition, of at least one ester which is liquid at room temperature comprising at least two hydrocarbon chains, each hydrocarbon chain independently containing at least 10 carbon atoms, the said ester containing no hydroxyl groups and having a wettability ranging from 5 minutes to 10 minutes,
  (ii) the possible difference to 100% by weight, relative to the total weight of the binder composition, of at least one fatty substance which is compatible with the said ester.

Advantageously, the binder composition may contain at least 30%, and preferably at least 45%, by weight of the ester, or of a mixture, relative to the total weight of the binder composition. According to one alternative embodiment of the invention, the binder composition may consist solely of the ester.

According to the invention, the hydrocarbon chains of the ester may preferably contain, independently, from 12 to 40 carbon atoms.

In the present description, the term liquid ester is understood to refer to an ester that is capable of flowing at room temperature.

The wettability of the ester according to the invention is determined according to the procedure described before the illustrative examples. It preferably ranges from 30 seconds to 10 minutes and more preferably from 50 seconds to 9 minutes.

Preferably, when the composition according to the invention is in the form of a compact powder, the wettability of the ester may advantageously range from 5 minutes to 10 minutes and preferably from 8 to 9 minutes. In this case, very good results in terms of cohesion of the compact powders are obtained with these esters.

Advantageously, the ester may be selected from glyceryl triisostearate, isocetyl stearate, stearoyloctyldecyl stearate, isodecyl laurate and a mixture thereof. Glyceryl triisostearate may preferably be used, in particular when the composition is in the form of a compact powder, to obtain good cohesion properties.

Obviously, the binder composition according to the invention may consist entirely of one or more esters in a mixture, as defined above.

In the present description, the term fatty substances which are compatible with the ester is understood to refer to any compound which is insoluble in water and whose mixture with the ester is clear and homogeneous after storage for 2 months at 45° C., that is to say that the mixture forms only a single phase with no appearance of cloudiness.

Preferably, the compatible fatty substance has a viscosity, at 25° C., ranging from $10^{-5}$ m$^2$/s to $10^{-3}$ m$^2$/s.

Preferably, the compatible fatty substance may be selected from phenyl silicones, ($C_6$–$C_{30}$)alkyl dimethicones, it being possible for the alkyl chain to be interrupted by an ester function, ($C_6$–$C_{30}$)alkoxy dimethicones, poly-α-olefins or a mixture thereof.

The phenyl silicones are preferably selected from phenyl silicone oils, in particular polyphenylmethylsiloxanes or phenyltrimethicones, or mixtures thereof, and in particular phenyl silicone oils corresponding to the formula (I) below:

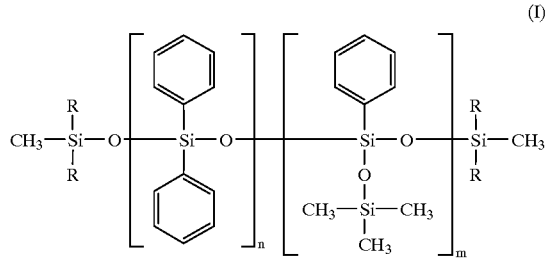

in which

R is a $C_1$–$C_{30}$ alkyl radical, an aryl radical or an aralkyl radical, n is an integer between 0 and 100, m is an integer between 0 and 100, with the proviso that the sum m+n is between 1 and 100.

Preferably, R is a methyl, ethyl, propyl, isopropyl, decyl, dodecyl or octadecyl radical or alternatively a phenyl, tolyl, benzyl or phenethyl radical.

Among these phenyl oils, mention may be made of the oil BELSIL PDM1000 from Wacker, the oils DC556 or SF558 from Dow Corning, the oil ABIL AV8853 from Goldschmidt or the oil SILBIONE 70633V30 from Rhône-Poulenc.

The poly-α-olefins may be, in particular:

of hydrogenated or non-hydrogenated polybutene type, and preferably hydrogenated or non-hydrogenated polyisobutene.

Preferably, isobutylene oligomers with a molecular weight of less than 1000 and mixtures thereof with poly-isobutylenes with a molecular weight of greater than 1000 and more preferably ranging from 1000 to 15000 are used.

As examples of poly-α-olefins which can be used in the context of the present invention, mention may be made more particularly of the products sold under the name PERM-ETHYL 99 A, 101 A, 102 A, 104 A (n=16) and 106 A (n=38) by the company Presperse Inc., or alternatively the products sold under the name ARLAMOL HD (n=3) by the company ICI (n denoting the degree of polymerization), of polyisoprene type, which are sold, for example, under the name SYNTHESQUAL by the company Vevy;

of hydrogenated or non-hydrogenated polydecene type, which are sold, for example, under the names ETH-YLFLO by the company Ethyl Corp. and ARLAMOL PAO by the company ICI.

More particularly, phenyl silicones and advantageously phenyltrimethicones and polydecenes can be used as compatible fatty substance.

According to a preferred embodiment of the composition according to the invention, the binder composition comprises from 30 to 50% of the ester and from 50 to 70% of compatible fatty substance.

In addition to the binder composition, the binder may comprise a level, not exceeding 10% by weight relative to the total weight of binder, of other commonly used fatty substances, such as waxes of plant, animal or synthetic origin, fluoro oils or lanolin. These additional fatty substances are selected so as not to modify the advantageous properties of dispersion and of cohesion imparted by the binder composition according to the invention.

According to a preferred embodiment of the composition according to the invention, the binder comprises 100% by weight of the binder composition.

The binder may be present in an amount ranging from 1 to 30%, preferably 3 to 25%, by weight relative to the total weight of the composition.

The pulverulent compounds present in the composition may be selected from pigments, pearlescent agents and/or fillers. They are preferably present in an amount ranging from 70 to 99% by weight of the composition.

Among the pigments, which are preferably present in an amount ranging from 0.5 to 80% by weight of the composition, mention may be made of inorganic pigments such as titanium dioxide (rutile or anatase) which is optionally surface-treated, black, yellow and red iron oxides, manganese violet, ultramarine blue, ultramarine violet, anhydrous or hydrated chromium oxide and ferric blue. The organic pigments may be selected from carbon black, pigments of D & C type, and lakes based on cochineal carmine.

The pearlescent agents, which are preferably present in an amount ranging from 0 to 50% by weight of the composition, may be selected from pearlescent pigments such as mica coated with organic and/or inorganic pigments such as titanium oxide or bismuth oxychloride, titanium mica coated with organic and/or inorganic pigments such as iron oxides, ferric blue or chromium oxide, as well as pearlescent pigments based on bismuth oxychloride.

The fillers, which are preferably present in an amount ranging from 0.1 to 95% by weight in the composition, may be inorganic or organic and lamellar or spherical. Mention may be made of talc, mica, silica, kaolin, powders of nylon, of poly-β-alanine and of polyethylene, Teflon, lauroyllysine, starch, boron nitride, bismuth oxychloride, tetrafluoroethylene polymer powders, polymethyl methacrylate powders, polyurethane powders, polystyrene powders, polyester powders, hollow microspheres such as EXPANCEL (Nobel Industries), POLYTRAP (Dow Corning) and silicone resin microbeads (TOSPEARLS from Toshiba for example), zinc and titanium oxides, precipitated calcium carbonate, magnesium carbonate and hydrocarbonate, hydroxyapatite, hollow silica microspheres (Silica Beads from Maprecos) and glass or ceramic microcapsules; metal soaps derived from organic carboxylic acids having from 8 to 22 carbon atoms, preferably from 12 to 18 carbon atoms, for example zinc, magnesium or lithium stearate, zinc laurate or magnesium myristate.

The composition according to the invention may also comprise other additives which are commonly used, in particular, in the cosmetics field. These additives are selected on the basis of the desired effect for the final composition when it is applied, such as the covering power, the transparency, the matte effect and/or the satiny appearance. Mention may be made, without limitation, of sunscreens, vitamins, moisturizers, cicatrizing agents, softeners, emollients, antiacne agents, fragrances, antiseptic agents or astringents which are used in particular in deodorant powders or in baby powders.

The processes for manufacturing the compositions according to the invention do not differ in any way from the processes used conventionally, in particular in cosmetics, which are entirely known to those skilled in the art.

The composition according to the invention is preferably in anhydrous form.

In the present description, the term anhydrous composition is understood to refer to a composition which is free of water without, however, excluding the water of crystallization of the ingredients used or the water resulting from the humidity of the ambient air, which may be present in the composition, in particular during storage.

The compact composition according to the invention may in particular be a compacted powder or alternatively a cast powder.

The compacted powder may be prepared, in a known manner, by pressing the powder, in particular using a compacting press.

The cast powder may be prepared by suspending the constituents of the powder in a solvent (for example, water, hexane, isopropanol, ethanol, etc.), after which the mixture is cast in a cupel and the solvent is evaporated off.

When it is desired to prepare a composition based on plaster/gypsum, it may be prepared by forming a mixture of the powders and the fatty substances in an aqueous phase, after which the mixture obtained is cast and left to dry and set to a solid.

The composition according to the invention may be used as a blusher, an eyeshadow, a foundation or alternatively as a perfumed or deodorant body powder, including a foot powder.

Procedure for Determining the Wettability of the Esters

A powder having the following composition was prepared:

| Phase A | |
|---|---|
| talc (15 M 00 from Luzenac) | 24.6 g |
| mica (MICA CONCORD 1000 from Sciama) | 23.55 g |
| bismuth oxychloride (PEARL-GLO UVR from ISP) | 8.55 g |
| zinc stearate (ZINC STEARATE S from Tissco) | 3.2 g |
| polyamide-12 (ORGASOL 2002 D Nat Extra Cos from Atochem) | 21.4 g |
| titanium dioxide (HOMBITAN ANATASE FF Pharma from Sachtleben) | 2.15 g |
| Phase B | |
| black ironoxide (BLACK SICOMET 85 E 172 from BASF) | 6.4 g |
| red iron oxide (BROWN SICOMET ZP 3569 from BASF) | 6.95 g |
| yellow iron oxide (BLACK SICOMET 10 E 172 from BASF) | 3.2 g |

The constituents of the formula were weighed out and mixed together efficiently for 15 minutes with a high-speed mixer until a homogeneous mixture was obtained. The powder was then screened through a 160 μm screen.

2.5 g of prepared powder were weighed out exactly and introduced into a compacting matrix fitted with a cupel having the following dimensions:

length: 28 mm, width: 23 mm, height: 3.5 mm.

The powder was then compacted at a pressure of $10^7$ Pa—100 bar—(piston diameter: 27 mm), using a Kemwall-type manual compacting press fitted with a compacting frame, to obtain a hardness of 72 Shore A measured with a Zwick durometer.

One drop of the test liquid was placed on the powder thus compacted using a clean Pasteur pipette. The drop was placed on the surface of the compacted powder after checking visually that no rough areas were visible at the surface.

The time taken for the drop to become completely absorbed on the surface of the compact was then measured, the absorption being performed during matting of the surface.

The time measured corresponds to the wettability value of the liquid tested.

Examples illustrating the present invention without, however, limiting it will now be given.

EXAMPLES

Comparative Examples

Comparative Example I 16 different esters were compared on the basis of their properties of dispersion and cohesion of compacted powders.

A base formula I was first prepared, this formula having the following composition:

Base formula I

| Phase A: | |
|---|---|
| talc | 23 g |
| bismuth oxychloride | 8 g |
| zinc stearate | 3 g |
| mica | 22 g |
| polyamide-12 powder | 20 g |
| titanium dioxide | 2 g |
| Phase B: | |
| black iron oxide | 6 g |
| red iron oxide | 6.5 g |
| yellow iron oxide | 3 g |
| Phase C: | |
| test ester | 6.5 g |

The base composition was prepared by mixing together the constituents of phase A and phase B, then phase C (ester) was added dropwise and further mixing was carried out. 2 g of powder were then screened and compacted in a metal cupel having the following dimensions:

length: 28 mm, width: 22 mm, height: 3.5 mm, at a pressure of $6\times10^6$ Pa—60 bar—(piston diameter: 27 mm), using a Kemwall-type manual compacting press.

The quality of the dispersion of the compacted powder obtained was then evaluated for each test ester, according to the following criteria:

good dispersion: uniform colour with no presence of white spots or marks moderate dispersion: presence of many small white spots and/or marks on the surface of the compact very poor dispersion: very visible marks The cohesion of the compact was also measured by measuring the loss of mass of powder after 10 standardized drops from a height of 20 cm. The cohesion was evaluated either according to the following rating:

++: very good cohesion
+: adequate cohesion
0: poor cohesion
00: very poor cohesion or by determining the percentage loss of mass of powder.

The following results were obtained, where * indicates an ester according to the invention:

| ESTER | WETTABILITY | DISPERSION | COHESION |
|---|---|---|---|
| glyceryl triiso-stearate (*) | 8 min 35 sec | good | 0.17% |
| isocetyl stearate (*) | 53 sec | good | 1.40% |
| octyldodecyl-stearoyl stearate (*) | 3 min 30 sec | good | 0.17% |
| isodecyl laurate (*) | 39 sec | good | not measured |
| 2-ethylhexyl palmitate | 25 sec | moderate | 00 |
| 2-ethylhexyl stearate | 30 sec | moderate | 00 |
| diisopropyl adipate | 7 sec | moderate | 00 |
| isononyl isononanoate | 9 sec | moderate | ++ |
| isopropyl palmitate | 14 sec | moderate | 00 |
| isostearyl neopentanoate | 28 sec | moderate | ++ |
| octyldodecyl neopentanoate | 35 sec | moderate | + |
| neopentyl glycol octanoate | 29 sec | moderate | 0 |
| pentaerythrityl tetraisostearate | 12 min 45 sec | very poor | 00 |
| propylene glycol isostearate | 1 min 44 sec | very poor | ++ |
| glyceryl isostearate | 33 min 30 sec | very poor | ++ |
| polyglyceryl diisostearate (3 units of glycerol) | 1 h 30 min | very poor | ++ |

It was observed that the esters according to the invention made it possible to obtain compacted powders having good dispersion and good cohesion of the powders. Among these esters, the compacted composition comprising glyceryl triisostearate was of better cohesion than the compacted composition comprising isocetyl stearate.

Comparative Example II

Three esters were compared on the basis of their property of cohesion in a compacted formula having the base composition II below:

Base formula II

| Phase A: | |
|---|---|
| talc | 44.2 g |
| Phase B: | |
| yellow iron oxide | 1.8 g |
| black iron oxide | 3 g |
| chromium oxide | 1 g |
| Phase C1: | |
| titanium oxide mica | 40 g |
| Phase C2: | |
| test ester | 10 g |

Base formula II was compacted under the same conditions as those used for base formula I of Comparative Example I. The percentage loss of mass of powder was determined under the same conditions as those described in Comparative Example I.

The following results were obtained:

| ESTER | WETTABILITY | COHESION |
|---|---|---|
| glyceryl triisostearate | 8 min 35 sec | 18.6% |
| isocetyl stearate | 53 sec | 21.0% |
| octyldodecylstearoyl stearate | 3 min 30 sec | 20.5% |

It was observed that the loss of product was least for the compacted composition comprising glyceryl triisostearate. This ester therefore has the best property of cohesion.

Comparative Example III 4 compacted compositions (A, A', B and B') were prepared.

Composition A was the same as base formula I in which phase C comprised 3.25 g of glyceryl triisostearate and 3.25 g of polydecene.

Composition B was the same as base formula II in which phase C2 comprised 5 g of glyceryl triisostearate and 5 g of polydecene.

Compositions A' and B' were similar to compositions A and B respectively, but the glyceryl triisostearate was replaced by the same amount of isocetyl isostearate.

The polydecene used is sold under the name SILKFLO 366 NF by the company Amoco Chemical.

The compositions were compacted under the same conditions as those described in Comparative Examples I and II. The percentage loss of mass of powder was determined and the following results were obtained:

| Composition | Binder | Cohesion |
|---|---|---|
| Composition A | glyceryl triisostearate/ polydecene (50/50) | 0.17% |
| Composition A' | isocetyl isostearate/ polydecene (50/50) | 0.75% |
| Composition B | glyceryl triisostearate/ polydecene (50/50) | 12.6% |
| Composition B' | isocetyl isostearate/ polydecene (50/50) | 14% |

It was observed that for compositions A and B according to the invention, the percentage loss of mass of powder was lower than that obtained for compositions A' and B' respectively. Thus, when combined with a polydecene, glyceryl triisostearate retains its good properties of cohesion.

Example 1

A blusher having the following composition was prepared:

| Phase A: | |
|---|---|
| calcium sulphate semihydrate | 24 g |
| talc | 22.2 g |
| lauroyllysine coated talc | 12 g |
| silica beads | 8 g |
| mica | 22 g |

-continued

| Phase B: | |
|---|---|
| red iron oxide | 3.5 g |
| yellow iron oxide | 1 g |
| black iron oxide | 0.5 g |
| Phase C: | |
| glyceryl triisostearate | 3 g |
| phenyltrimethylsiloxytrisiloxane | 3 g |
| (DC 556 Fluid Cosmetic from Dow Corning) | |
| polysorbate-20 | 0.8 g |

The composition was prepared by mixing together the constituents of phase A and phase B, after which phase C was added dropwise and further mixing was carried out. The mixture obtained was then dispersed in 70 parts of water per 100 parts of powder mixture to obtain a fluid paste.

The paste was then cast in a concave mould.

After left to stand for 2 hours at room temperature, the product was heated in an oven at 45 degrees for 12 hours. The product was then removed from the mould after drying. In the dry product, the calcium sulphate is in dihydrate form (water of crystallization).

Good dispersion of the pulverulent compounds was observed in the product obtained. The powder was easy to crumble and feels soft when applied to the cheeks.

Example 2

A compacted eyeshadow having the following composition was prepared:

| Phase A | |
|---|---|
| talc | 63 g |
| silicone coated mica | 8 g |
| polyethylene powder | 5 g |
| titanium mica | 10 g |
| Phase B | |
| red iron oxide | 3 g |
| ultramarine blue | 3 g |
| Phase C | |
| isocetyl stearate | 8 g |

The constituents of phase A and phase B were mixed together, after which phase C was added dropwise and further mixing was carried out. After screening, the powder was compacted in a metal cupel. An eyeshadow having good dispersion of the powders and good cohesion was obtained.

Example 3

A compacted eyeshadow having the following composition was prepared:

| Phase A | |
|---|---|
| talc | 20 g |
| mica | 10 g |
| bismuth oxychloride | 8 g |
| titanium mica | 40 g |

-continued

| Phase B | |
|---|---|
| anhydrous chromium oxide | 6 g |
| ultramarine blue | 2 g |
| Phase C | |
| glyceryl triisostearate | 7 g |
| hydrogenated polydecene | 7 g |
| (Silkflo 366 NF from Albemarle) | |

The composition was prepared according to the same procedure as in Example 2. An eyeshadow having good dispersion of the powders and good cohesion was obtained.

Example 4

A compacted blusher having the following composition was prepared:

| Phase A | |
|---|---|
| talc | 67.8 g |
| mica | 15 g |
| polymethyl methacrylate powder | 6 g |
| zinc laurate | 2 g |
| Phase B | |
| manganese violet | 1.2 g |
| red iron oxide | 0.9 g |
| black iron oxide | 0.1 g |
| Phase C | |
| isocetyl stearate | 2.1 g |
| hydrogenated polydecene | 4.9 g |

The composition was prepared according to the same procedure as in Example 2. A blusher having good dispersion of the powders and good cohesion was obtained.

Example 5

A free face powder having the following composition was prepared:

| Phase A | |
|---|---|
| mica | 65.05 g |
| titanium mica-yellow iron oxide | 8 g |
| polyamide-12 powder | 20 g |
| sodium hyaluronate | 0.1 g |
| zinc stearate | 3 g |
| Phase B | |
| yellow iron oxide | 0.4 g |
| red iron oxide | 0.3 g |
| black iron oxide | 0.15 g |
| Phase C | |
| phenyltrimethylsiloxy trisiloxane | 1.8 g |
| glyceryl triisostearate | 1.2 g |

The composition was prepared according to the same procedure as in Example 2, the powder not being compacted but used in free form.

It was seen that the pulverulent compounds were well dispersed and that the powder was applied easily to the face and had good staying power.

Example 6

A compacted face powder having the following composition was prepared:

| Phase A | |
|---|---|
| sericite | 66.8 g |
| mica | 15 g |
| polyamide-12 powder | 6 g |
| titanium dioxide | 2 g |
| Phase B | |
| yellow iron oxide | 2.5 g |
| red iron oxide | 1.2 g |
| black iron oxide | 0.5 g |
| Phase C | |
| isocetyl stearate | 2.4 g |
| hydrogenated polydecene | 2.4 g |
| phenyltrimethylsiloxytrisiloxane | 1.2 g |

The composition was prepared according to the same procedure as in Example 2. A compacted face powder having good dispersion of the powder and good cohesion was obtained.

Example 7

A compacted face powder having the following composition was prepared:

| Phase A | |
|---|---|
| silicone coated talc | 20 g |
| mica | 35 g |
| titanium dioxide | 4.5 g |
| talc | 27.3 g |
| zinc stearate | 3 g |
| Phase B | |
| yellow iron oxide | 1.6 g |
| red iron oxide | 0.9 g |
| black iron oxide | 0.4 g |
| preserving agents | 0.3 g |
| Phase C | |
| isodecyl laurate | 4.9 g |
| polyisoprene (Synthesqual from Vevy) | 2.1 g |

The composition was prepared according to the same procedure as in Example 2. A compacted face powder having good dispersion of the powder and good cohesion was obtained. The compacted powder was able to be crumbled while dry with a standard applicator (brush or sponge-tipped applicator) or alternatively using a wet sponge. It was seen that the powder applied easily to the skin and had a soft feel.

We claim:

1. A method for obtaining a dispersed powder, said method comprising the step of including in an anhydrous composition in powder form comprising at least one pulverulent compound, a binder composition in an amount effective to disperse said anhydrous composition in powder form, wherein said binder composition comprises:

(i) at least 20% by weight, relative to the total weight of the binder composition, of at least one ester which is liquid at room temperature, wherein said at least one ester comprises at least two hydrocarbon chains, each hydrocarbon chain independently containing at least 10 carbon atoms, and wherein said at least one ester does not contain any hydroxyl groups, and further wherein said at least one ester has a wettability ranging from 30 seconds to 10 minutes, and (ii) when said at least one ester comprises less than 100% by weight of said binder composition, said binder composition further comprises at least one fatty substance which is compatible with said ester, wherein said at least one fatty substance is present in an amount by weight relative to the total weight of the binder composition such that the amount of said at least one ester and the amount of said at least one fatty substance total 100% of said binder composition.

2. A method for improving the solidity and/or strength of an anhydrous composition in the form of a compact powder comprising at least one pulverulent compound, said method comprising the step of including in said anhydrous composition a binder composition in an amount effective to improve the solidity and/or strength of said anhydrous composition, wherein said binder composition comprises:

(i) at least 20% by weight, relative to the total weight of the binder composition, of at least one ester which is liquid at room temperature, wherein said at least one ester comprises at least two hydrocarbon chains, each hydrocarbon chain independently containing at least 10 carbon atoms, and wherein said at least one ester does not contain any hydroxyl groups, and further wherein said at least one ester has a wettability ranging from 30 seconds to 10 minutes, and (ii) when said at least one ester comprises less than 100% by weight of said binder composition, said binder composition further comprises at least one fatty substance which is compatible with said ester, wherein said at least one fatty substance is present in an amount by weight relative to the total weight of the binder composition such that the amount of said at least one ester and the amount of said at least one fatty substance together total 100% of said binder composition.

3. A method according to claim 2, wherein said strength is impact strength.

4. A method according to claim 1, wherein said at least one ester has a wettability ranging from 50 seconds to 9 minutes.

5. A method according to claim 4, wherein said at least one ester has a wettability ranging from 5 minutes to 9 minutes.

6. A method according to claim 5, wherein said at least one ester has a wettability ranging from 8 minutes to 9 minutes.

7. A method according to claim 1, wherein said at least two hydrocarbon chains each independently contain from 12 to 40 carbon atoms.

8. A method according to claim 1, wherein said at least one ester is glyceryl triisostearate, isocetyl stearate, stearoyloctyldecyl stearate, isodecyl laurate, or a mixture thereof.

9. A method according to claim 8, wherein said at least one ester is glyceryl triisostearate.

10. A method according to claim 1, wherein said at least one fatty substance is a phenyl silicone; a $(C_6-C_{30})$alkyl dimethicone wherein the alkyl chain of said dimethicone is optionally interrupted by an ester function; a $(C_6-C_{30})$ alkoxy dimethicone; a poly-α-olefin; or a mixture thereof.

11. A method according to claim 1, wherein said at least one fatty substance has a viscosity, at 25° C., ranging from $10^6$ m$^2$/s to $10^3$ m$^2$/s.

12. A method according to claim 1, wherein said at least one fatty substance is selected from polybutene poly-α-olefins, polydecene poly-α-olefins, and phenyl silicones of formula (I):

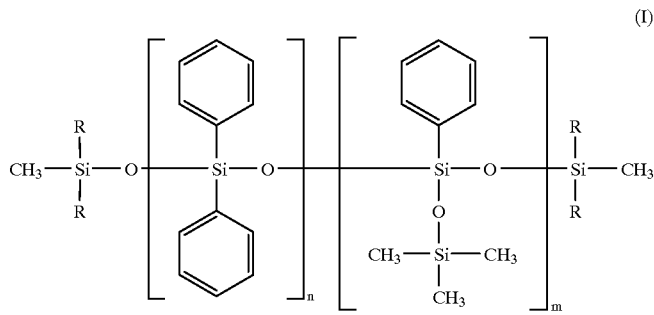

(I)

wherein
each R independently is a $C_1$–$C_{30}$ alkyl radical, an aryl radical or an aralkyl radical,
n is an integer ranging from 0 to 100, and
m is an integer ranging from 0 to 100,
and wherein the sum m+n ranges from 1 to 100.

13. A method according to claim 1, wherein said at least one pulverulent compound is a pigment, filler, pearlescent agent, or a mixture thereof.

14. A method according to claim 1, wherein said at least one pulverulent compound is present in an amount ranging from 70% to 99% by weight relative to the total weight of the composition.

15. An anhydrous composition in compact powder form comprising at least one binder and at least one pulverulent compound, wherein said at least one binder comprises at least 90% by weight of a binder composition comprising:

(i) at least 20% by weight, relative to the total weight of the binder composition, of at least one ester which is liquid at room temperature, wherein said at least one ester comprises at least two hydrocarbon chains, each hydrocarbon chain independently containing at least 10 carbon atoms, and wherein said at least one ester does not contain any hydroxyl groups, and further wherein said at least one ester has a wettability ranging from 5 minutes to 10 minutes, and (ii) when said at least one ester comprises less than 100% by weight of said binder composition, said binder composition further comprises at least one fatty substance which is compatible with said ester, wherein said at least one fatty substance is present in an amount by weight relative to the total weight of the binder composition such that the amount of said at least one ester and the amount of said at least one fatty substance together total 100% of said binder composition.

16. A composition according to claim 15, wherein said at least one ester has a wettability ranging from 8 minutes to 9 minutes.

17. A composition according to claim 15, wherein said at least one ester is glyceryl triisostearate.

18. A composition according to claim 15, wherein said at least one fatty substance is a phenyl silicone, a ($C_6$–$C_{30}$) alkyl dimethicone wherein the alkyl chain of said dimethicone is optionally interrupted by an ester function, a ($C_6$–$C_{30}$)alkoxy dimethicone, a poly-α-olefin, or a mixture thereof.

19. A composition according to claim 15, wherein said at least one fatty substance is selected from polybutene poly-α-olefins, polydecene poly-α-olefins, and phenyl silicones of formula (I):

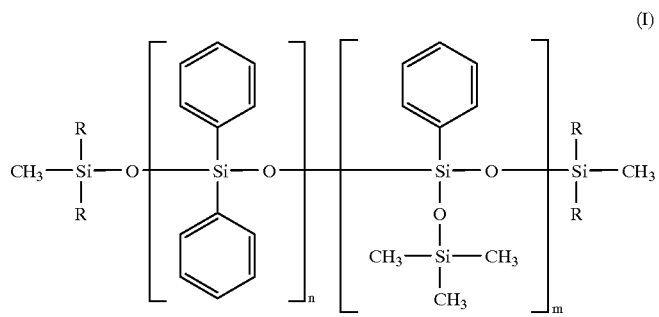

(I)

wherein
each R independently is a $C_1$–$C_{30}$ alkyl radical, an aryl radical or an aralkyl radical,
n is an integer ranging from 0 to 100, and
m is an integer ranging from 0 to 100,
and wherein the sum m+n ranges from 1 to 100.

20. A composition according to claim 15, wherein said at least one binder is present in an amount ranging from 1% to 30% by weight relative to the total weight of the composition.

21. A composition according to claim 20, wherein said at least one binder is present in an amount ranging from 3% to 25% by weight relative to the total weight of the composition.

22. A composition according to claim 15, wherein said at least one pulverulent compound is present in an amount ranging from 70% to 99% by weight relative to the total weight of the composition.

23. A composition according to claim 15, further comprising at least one additive, wherein said at least one additive is a sunscreen, vitamin, moisturizer, cicatrizing agent, softener, emollient, fragrance, antiseptic agent or astringent.

24. A composition according to claim 15, wherein said composition is in the form of a blusher, an eyeshadow, a foundation, a free powder for making up the face or a body powder.

* * * * *

UNITED STATES PATENT AND TRADEMARK OFFICE
CERTIFICATE OF CORRECTION

PATENT NO.: 5,928,652

DATED: July 27, 1999

INVENTOR(S): Sophie Bodelin-LeComte and Béatrice DeFossez

It is certified that an error appears in the above-identified patent and that said Letters Patent is hereby corrected as shown below:

ON THE TITLE PAGE:

Title page, item [54], "Inventor: Sophie Bodelin-LeComte, Vanves, France" should read -- Inventors: Sophie Bodelin-LeComte, Vanves; Béatrice DeFossez, Paris, both of France--.

Signed and Sealed this

Fourteenth Day of December, 1999

Q. TODD DICKINSON

*Attest:*

*Attesting Officer*    Acting Commissioner of Patents and Trademarks